(12) United States Patent
Lu et al.

(10) Patent No.: US 10,595,727 B2
(45) Date of Patent: Mar. 24, 2020

(54) MACHINE LEARNING-BASED SEGMENTATION FOR CARDIAC MEDICAL IMAGING

(71) Applicant: Siemens Healthcare GmbH, Erlangen OT (DE)

(72) Inventors: Xiaoguang Lu, West Windsor, NJ (US); Monami Banerjee, Gainesville, FL (US)

(73) Assignee: Siemens Healthcare GmbH, Erlangen (DE)

(*) Notice: Subject to any disclaimer, the term of this patent is extended or adjusted under 35 U.S.C. 154(b) by 185 days.

(21) Appl. No.: 15/879,486

(22) Filed: Jan. 25, 2018

(65) Prior Publication Data
US 2019/0223725 A1 Jul. 25, 2019

(51) Int. Cl.
*A61B 5/00* (2006.01)
*G06N 3/08* (2006.01)
*A61B 6/00* (2006.01)
*A61B 6/03* (2006.01)
*G06T 7/11* (2017.01)
*G06T 7/00* (2017.01)

(52) U.S. Cl.
CPC ............ *A61B 5/0044* (2013.01); *A61B 6/032* (2013.01); *A61B 6/507* (2013.01); *G06N 3/08* (2013.01); *G06T 7/0012* (2013.01); *G06T 7/11* (2017.01); *G06T 2207/10081* (2013.01); *G06T 2207/10088* (2013.01); *G06T 2207/10104* (2013.01); *G06T 2207/10108* (2013.01); *G06T 2207/10121* (2013.01); *G06T 2207/10132* (2013.01); *G06T 2207/20081* (2013.01); *G06T 2207/20084* (2013.01); *G06T 2207/30048* (2013.01); *G06T 2207/30101* (2013.01)

(58) Field of Classification Search
CPC . G06T 2207/20081; G06T 2207/30048; G06T 7/0012; G06T 2207/20084; G06T 2207/10088; G06T 7/11; G06N 3/08
See application file for complete search history.

(56) References Cited

U.S. PATENT DOCUMENTS

2017/0360411 A1* 12/2017 Rothberg ............... A61B 8/085
2017/0360412 A1* 12/2017 Rothberg ............... A61B 8/085
2018/0218502 A1* 8/2018 Golden .................... G06T 7/10

OTHER PUBLICATIONS

J. Ker, L. Wang, J. Rao and T. Lim, "Deep Learning Applications in Medical Image Analysis," in IEEE Access, vol. 6, pp. 9375-9389, 2018. doi: 10.1109/ACCESS.2017.2788044 (Year: 2017).*
M. F. Stollenga, W. Byeon, M. Liwicki, and J. Schmidhuber, "Parallel multi-dimensional LSTM, with application to fast biomedical volumetric image segmentation," in Proc. Adv. Neural Inf. Process. Syst., 2015, pp. 2998-3006 (Year: 2015).*

(Continued)

*Primary Examiner* — Ross Varndell

(57) ABSTRACT

For heart segmentation in magnetic resonance or other medical imaging, deep learning trains a neural network. The neural network, such as U-net, includes at least one long-short-term memory (LSTM), such as a convolutional LSTM. The LSTM incorporates the temporal characteristics with the spatial to improve accuracy of the segmentation by the machine-learnt network.

20 Claims, 5 Drawing Sheets

(56) References Cited

OTHER PUBLICATIONS

Jianxu Chen, Lin Yang, Yizhe Zhang, Mark Alber, and Danny Z Chen, Combining fully convolutional and recurrent neural networks for 3d biomedical image segmentation, Advances in Neural Information Processing Systems 29, Curran Associates, Inc . . . 2016, pp. 3036-3044. (Year: 2016).*

Anh Ngo, Tuan, et al. "Fully automated non-rigid segmentation with distance regularized level set evolution initialized and constrained by deep-structured inference." Proceedings of the IEEE Conference on Computer Vision and Pattern Recognition. 2014.

Avendi, M. R., et al. "Fully automatic segmentation of heart chambers in cardiac MRI using deep learning." Journal of Cardiovascular Magnetic Resonance 18.1 (2016): p. 351.

Grosgeorge, Damien, et al. "Graph cut segmentation with a statistical shape model in cardiac MRI." Computer Vision and Image Understanding 117.9 (2013): 1027-1035.

Hu, Huaifei, et al. "Automatic segmentation of the left ventricle in cardiac MRI using local binary fitting model and dynamic programming techniques." PloS one 9.12 (2014): e114760.

Huang, Su, et al. "An image-based comprehensive approach for automatic segmentation of left ventricle from cardiac short axis cine MR images." Journal of digital imaging 24.4 (2011): 598-608.

Peng, Peng, et al. "A review of heart chamber segmentation for structural and functional analysis using cardiac magnetic resonance imaging." Magnetic Resonance Materials in Physics, Biology and Medicine 29.2 (2016): 155-195.

Petitjean, Caroline, and Jean-Nicolas Dacher. "A review of segmentation methods in short axis cardiac MR images." Medical image analysis 15.2 (2011): 169-184.

Poudel, Rudra PK, et al. "Recurrent fully convolutional neural networks for multi-slice mri cardiac segmentation." International Workshop on Reconstruction and Analysis of Moving Body Organs. Springer, Cham, 2016.

Ronneberger, Olaf, et al. "U-net: Convolutional networks for biomedical image segmentation." International Conference on Medical Image Computing and Computer-Assisted Intervention. Springer, Cham, 2015.

Tran, Phi Vu. "A fully convolutional neural network for cardiac segmentation in short-axis MRI." arXiv preprint arXiv:1604.00494 (2016).

Long, Jonathan, Evan Shelhamer, and Trevor Darrell. "Fully convolutional networks for semantic segmentation." Proceedings of the IEEE Conference on Computer Vision and Pattern Recognition. 2015.

Zotti, Clément, et al. "GridNet with automatic shape prior registration for automatic MRI cardiac segmentation." arXiv preprint arXiv:1705.08943 (2017).

* cited by examiner

MACHINE LEARNING-BASED SEGMENTATION FOR CARDIAC MEDICAL IMAGING

BACKGROUND

The present embodiments relate to segmentation and machine learning of the segmentation, such as segmenting the left ventricle in magnetic resonance (MR) imaging.

Spatiotemporal images are routinely acquired for dynamic quantification of organ function. For example, MR imaging routinely acquires a stack of short-axis cardiac slices to image the entire left ventricle over time. Such images are used to assess an organ across multiple time points, at various locations. Segmentation of the left ventricle is used for computing several clinical indices of cardiovascular disease, such as ventricular volume, ejection fraction, left ventricular mass and wall thickness, as well as analyses of the wall motion abnormalities.

Current standard clinical practice for left ventricle segmentation is manual delineation, which is tedious, labor intensive, and prone to intra and inter observer variability. In one approach for automated segmentation, machine training is applied based on manually defined features. The performance depends on the high-level features. In another approach, the deep machine training learns task-specific image features through the annotation of large representative datasets in a fully automated fashion. For example, a fully convolutional segmentation model does not need explicit construction of task specific features. U-Net is a convolutional neural network with an architecture having a encoding path to capture context and a symmetric decoding path that enables end-to-end learning from fewer images. Both approaches for automated left ventricle segmentation involve many challenges: high class imbalance; inhomogeneity in intensity; considerable variability in the shape of the heart chambers across patients; variability in the shape across different views; and variability across different pathological cases. Greater accuracy in segmentation is desired.

SUMMARY

Systems, methods, and computer readable media are provided for heart segmentation in MR or other medical imaging. Deep learning trains a neural network. The neural network, such as U-net, integrated with at least one long-short-term memory (LSTM), such as a convolutional LSTM. The LSTM incorporates the temporal characteristics along with convolutional modeling the spatial properties to improve accuracy of the segmentation by the machine-learnt network.

In a first aspect, a method is provided for heart segmentation with a magnetic resonance imaging system. An MR imaging system scans a heart of a patient over time. A machine-learnt network detects a heart region represented in scan data from the scanning. The machine-learnt network is a convolutional to transposed-convolutional network with a convolutional long-short-term memory network. An image with information that is a function of the detected heart region is generated.

In a second aspect, a medical imaging system is provided for heart segmentation. A medical scanner is configured to scan a cardiac region of a patient over time. An image processor is configured to apply a machine-learnt detector to data from the scan. The machine-learnt detector has an architecture including convolutional and transposed-convolutional layers in a pyramid and a long-short-term memory layer. The machine-learnt detector is configured to output a heart segmentation as represented in the data from the scan. A display is configured to display a medical image with an annotation based on the output.

In a third aspect, a method is provided for machine training for heart segmentation. A neural network arrangement with a convolutional long-short-term memory architecture is defined. A machine trains the neural network arrangement with training data having ground truth segmentation of the heart segmentation in spatiotemporal images. The neural network as trained is stored.

Any one or more of the aspects described above may be used alone or in combination. These and other aspects, features and advantages will become apparent from the following detailed description of preferred embodiments, which is to be read in connection with the accompanying drawings. The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the embodiments. Moreover, in the figures, like reference numerals designate corresponding parts throughout the different views.

DETAILED DESCRIPTION OF EMBODIMENTS

Deep learning is used for analysis of spatiotemporal images. The resulting machine-learnt network is used for segmentation, such as for automatic quantification of cardiac MR examinations. The temporal information available in the data is accounted for in the architecture of the network. The predicted segmentation over time is refined and connected using LSTM. A deep network that models spatial as well as temporal information facilitates learning. Joint spatiotemporal analysis is provided for cardiac MR images utilizing a convolutional LSTM architecture.

Figure 1:
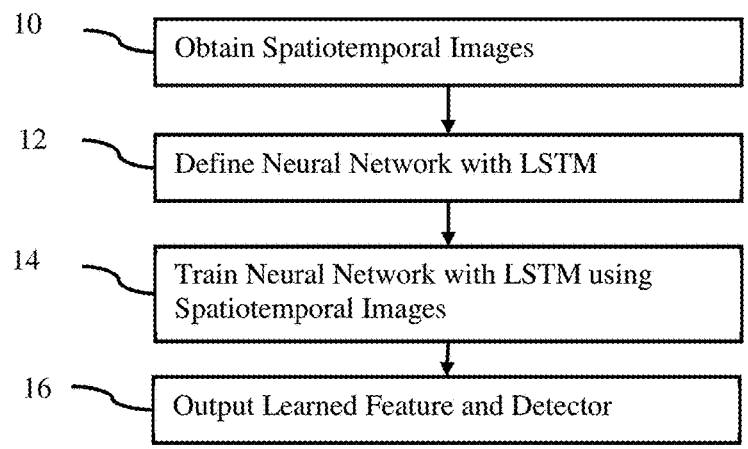
FIG. 1 is a flow chart diagram of one embodiment of a method for machine training for segmentation.
Figure 5:
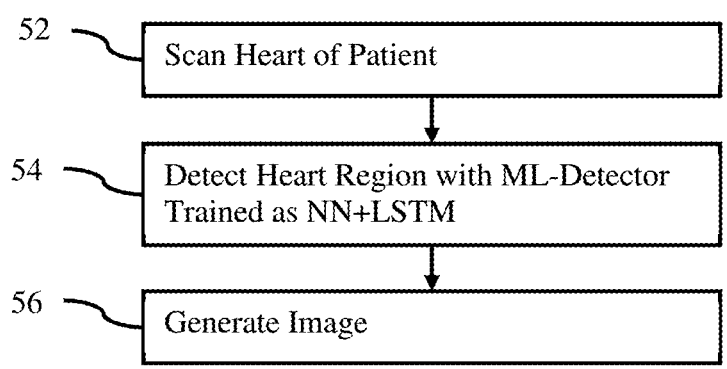
FIG. 5 is a flow chart diagram of one embodiment of a method for segmentation with an imaging system.

FIGS. 1 and 5 show methods for segmentation. The method for segmentation may be a method to learn how to detect the object or may be a method for detecting the object. FIG. 1 is directed to machine training of the network for segmentation. FIG. 5 is directed to application of a machine-learnt network. In both cases, a machine, such as an image processor, computer, or server, implements some or all the acts. The same or different machine is used for training and application. The system of FIG. 7 implements the methods in one embodiment, but other systems may be used.

A user may select the image files for application of the learnt network by the processor or select the images from which to learn features and train the network by a processor. Use of the machine allows processing large volumes (e.g., images of many pixels and/or many images) of information that may not be efficiently handled by humans, may be unrealistically handled by humans in the needed time frame, or may not even be possible by humans due to subtleties and/or timing. The machine may learn in a way different than a human to recognize the object in a way different than a human, improving diagnosis or treatment through diversity. Use of the architecture discussed herein may make the machine operate more quickly, use less memory, and/or provide better results in application and/or training than other automated approaches.

The methods are provided in the orders shown, but other orders may be provided. For FIG. 1, acts 12 and 14 may be performed as one act.

Additional, different or fewer acts may be provided. For example, act 16 of FIG. 1 is not provided. As another example, act 56 of FIG. 5 is not provided. In yet other examples, acts for capturing images and/or acts using detected information (e.g., quantification from a segmentation) are provided.

FIG. 1 shows a method for segmentation (i.e., object detection) through learning by an image processor or other machine. A deep architecture with LSTM used for training provides for accurate detection of the object.

In act 10, images of a same type of object (e.g., heart) are obtained. The images are obtained by data transfer, capture, and/or loading from memory. Any number of images of a same type of object is obtained, such as tens or hundreds of images of the object. The images are obtained with a same scanner or different scanners. The object as occurring in many different patients is included in the collection of images. Where the object occurs with different backgrounds, the images are of the object in the various backgrounds.

In one embodiment, the images are of the heart. For cardiac or heart segmentation, images of the hearts of various patients are obtained. Any number of images of each heart may be obtained. In other embodiments, the images are of other parts of the body, such as the torso or head. The object of interest in a medical image may be an organ (e.g., whole heart), part of an organ (e.g., left ventricle or other heart chamber), a cyst, a tumor, calcification, or other anomaly or lesion.

The images are captured using MR scanners. For example, gradient coils, a whole-body coil, and/or local coils generate a pulse sequence in a magnetic field created by a main magnet or coil. The whole-body coil or local coils receive signals responsive to the re-orientation of molecules shifted due to the pulse sequence. In other embodiments, the images are captured using x-ray, computed tomography, fluoroscopy, angiography, ultrasound, positron emission tomography, or single photon emission computed tomography.

The obtained images may be scan data used to generate an image on a display, such as a medical image being scan data from medical imaging. The obtained images may be from data being processed to generate an image, data formatted for display, or data that has been used to display. Scan data may be data with no or some image processing. For example, a displayed image may represent scan data after image processing. As another example, k-space data reconstructed to an object domain by a Fourier process without other filtering or change may be scan data.

The images represent volumes. Three-dimensional datasets are obtained. In alternative embodiments, two-dimensional datasets representing planes are obtained. In one embodiment, the medical images are long-axis cardiac images for 100 or other number of subjects.

For each subject or set of images, images representing the object over time are acquired. For cardiac imaging or imaging of organs that vary over time due to cardiac or breathing cycles, a sequence of images is acquired over one or more cycles. Fractional cycles may be used. For example, cardiac images for 100 subjects are acquired. For each subject, the images or sequence of images represent that subject through 1-6 cycles. For a given cycle, any number of images may be acquired, such as 18-35 sequential frames or images.

The medical images are used for training in act 14. The medical images may be used as received or may be pre-processed. In one embodiment of pre-processing, the received images are normalized. Since different settings, imaging systems, patients being scanned, and/or other variations in acquiring images may result in different offsets and/or dynamic ranges, normalization may result in more uniform representation of the object. Any normalization may be used, such as setting a maximum value to 1 with all other values linearly scaled between 0 and 1. Each volumetric scan or medical image is individually normalized.

The training data includes a ground truth indication of the object. The ground truth indication is a segmentation of the object, such as a marker, trace, border, or other segmentation of the left ventricle in each image. For example, a border of the left ventricle, binary mask of heart walls forming the left ventricle, or binary mask of the entire left ventricle may be used as the ground truth. The medical images, such as short or long axis cardiac CINE slices of the heart from cardiac scanning, are physician-annotated to add the ground truth. Alternatively, automatic segmentation is applied to add the ground truth.

In act 12, a neural network (e.g., deep learning) arrangement is defined. The definition is by configuration or programming of the learning. The number of layers or units, type of learning, and other characteristics of the network are controlled by the programmer or user. In other embodiments, one or more aspects (e.g., number of nodes, number of layers or units, or type of learning) are defined and selected by the machine during the learning.

Deep architectures include convolutional neural network (CNN) or deep belief nets (DBN), but other deep networks may be used. CNN learns feed-forward mapping functions while DBN learns a generative model of data. In addition, CNN uses shared weights for all local regions while DBN is a fully connected network (i.e., having different weights for all regions of an image). The training of CNN is entirely discriminative through back-propagation. DBN, on the other hand, employs the layer-wise unsupervised training (e.g., pre-training) followed by the discriminative refinement with back-propagation if necessary. In one embodiment, a CNN is used.

The neural network is defined as a plurality of sequential feature units or layers. Sequential is used to indicate the general flow of output feature values from one layer to input to a next layer. The information from the next layer is fed to a next layer, and so on until the final output. The layers may only feed forward or may be bi-directional, including some feedback to a previous layer. The nodes of each layer or unit may connect with all or only a sub-set of nodes of a previous or subsequent layer or unit.

Rather than pre-programming the features and trying to relate the features to attributes, the deep architecture is defined to learn the features at different levels of abstraction. The features are learned to reconstruct lower level features (i.e., features at a more abstract or compressed level). For example, features for reconstructing an image are learned. For a next unit, features for reconstructing the features of the previous unit are learned, providing more abstraction. Each node of the unit represents a feature. Different units are provided for learning different features.

Figure 2:
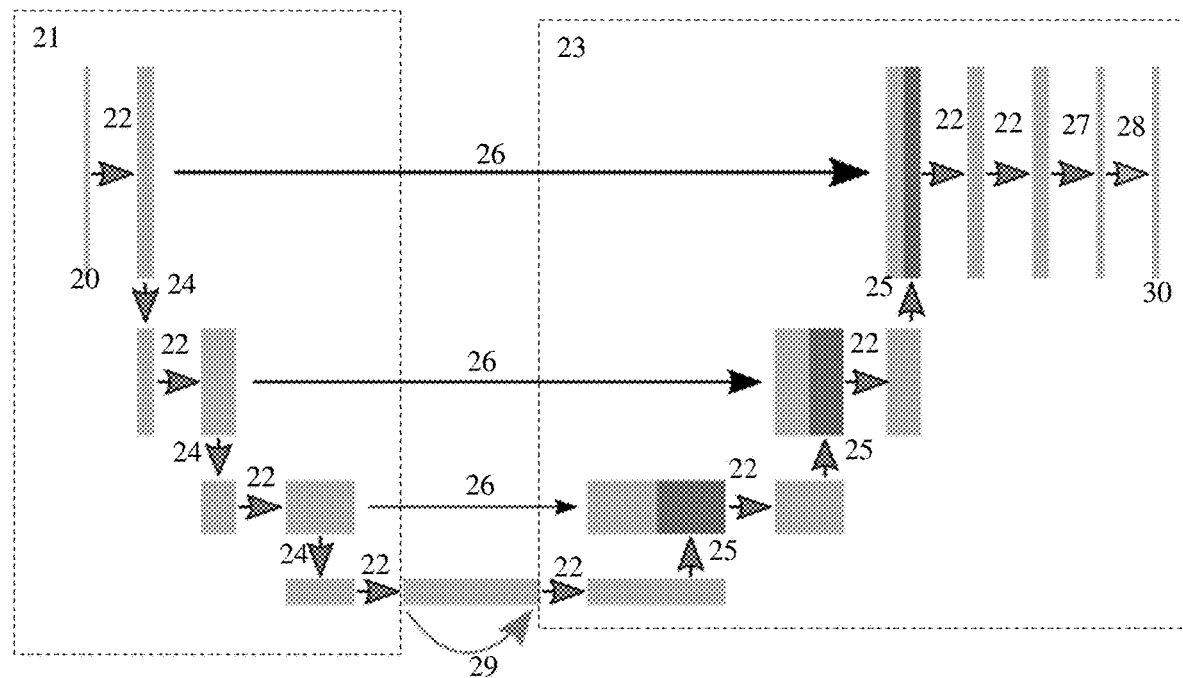
FIG. 2 illustrates an example neural network architecture using LSTM in sequence between an encoder output and a decoder input.

Within a unit or layer, any number of nodes is provided. For example, 100 nodes are provided. Any number of nodes may be used. A different number of nodes may be provided for different units or layers. Later or subsequent units may have more, fewer, or the same number of nodes. In general, for convolution, subsequent units have more abstraction. For example, the first unit provides features from the image, such as one node or feature being a line found in the image. The next unit combines lines, so that one of the nodes is a corner. The next unit may combine features (e.g., the corner and length of lines) from a previous unit so that the node provides a shape or building indication. In the example of FIG. 2, each unit 22, 24, 25, 27, 28 generically represents a plurality of nodes. For transposed-convolution, the level of abstraction reverses. Each unit or layer reduces the level of abstraction or compression.

The features of the nodes are learned by the machine using any building blocks. For example, auto-encoder (AE) or restricted Boltzmann machine (RBM) approaches are used. AE transforms data linearly, and then applies a non-linear rectification, like a sigmoid function. The objective function of AE is the expected mean square error between the input image and reconstructed images using the learned features. AE may be trained using stochastic gradient descent or other approach to learn, by a machine, the features leading to the best reconstruction. The objective function of RBM is an energy function. Exact computation of the likelihood term associated with RBM is intractable. Therefore, an approximate algorithm, such as contrastive-divergence based on k-step Gibb sampling or other, is used to train the RBM to reconstruct the image from features.

Training of AE or RBM is prone to over-fitting for high-dimensional input data. Sparsity or denoising techniques (e.g., sparse denoising AE (SDAE)) are employed to constrain the freedom of parameters and force learning of interesting structures within the data. Enforcing sparsity within hidden layers (i.e., only a small number of units in hidden layers are activated at one time) may also regularize the network. In other embodiments, at least one unit is a convolution with ReLU activation or is a batch normalization with a ReLU activation followed by a convolution layer (BN+LeakyRU+convolution). Different units may be of the same or different type.

Any neural network architecture may be used. In one embodiment for segmentation, a convolutional-transposed-convolutional network is used. One segment of layers or units applies convolution to increase abstractness or compression. The most abstract feature values are then output to another segment. The other segment of layers or units then applies transposed-convolution to decrease abstractness or compression, resulting in outputting of a segmentation or indication of class membership by location. In a further embodiment, the neural network is a U-net. An encoder (convolutional) and decoder (transposed-convolutional) network forms a "U" shape with one vertical being encoding, another vertical being decoding, and the connection between being passing features at a greatest level of compression or abstractness from the encoder to the decoder. Any now known or later developed U-net architectures may be used. Other fully convolutional networks may be used.

FIG. 2 shows one example definition of a network architecture. A U-net architecture is shown. The network architecture includes an encoder 21 and a decoder 23. The encoder 21 and decoder 23 are formed from various units 22, 24, 25, 27, 28. The architecture is a fully convolutional network, such that input samples of any size may be used. In alternative embodiments, the architecture is not fully convolutional. The architecture defines a neural network for deep learning.

In FIG. 2, the grey boxes represent data, such as the input images 20, the output segmentation mask 30, or intermediary collections of feature values. The arrows represent units or layers. For the convolution or encoder segment 21, convolutional units 22 (e.g., ReLU) and max pooling units 24 are used. For the transposed-convolution or decoder segment 23, convolutional units 22 (e.g., ReLU), transposed-convolution units 25 (e.g., ReLU), convolutional units 27 (e.g., Leaky ReLU), and a soft-max unit 28 are used. Each convolutional or transposed-convolutional unit 22, 25, and 27 contains a batch normalization layer and a ReLU activation followed by a 3×3×3 or other size convolutional layer. Other node arrangements may be used, such as AE and/or RBM. Other numbers of units, types of units, and/or arrangements of units may be used. For example, more or fewer units 22 and 27 are provided in the decoder segment 23 to generate the output segmentation for the least level of abstraction or compression.

The encoder 21 outputs features or values for features to the decoder 23. Bridging units may be used, such as treating the units 22 at the greatest level of abstraction as separate from the encoder segment 21 and/or the decoder segment 23. In other embodiments, the bridging is not provided, is included in the encoder 21, or is included in the decoder 23. Other intervening units may be provided between the encoder 21 and the decoder 23.

Other connections than at the bottom of the U-net (i.e., greatest level of abstraction) between the encoder 21 and the decoder 23 may be provided. Connections between different parts of the architecture at a same level of abstraction may be used. At each abstraction level of the decoder 23, the feature abstraction matches the corresponding encoder level. For example, the feature values output from each convolutional unit 22 in addition to the final or greatest compression of the encoder 21 are output to the next max-pooling unit 24 as well as to a convolutional unit 22 of the decoder 23 with a same level of abstraction. The arrows 26 show this concatenation as skip connections. The skip connections skip one or more units. These skip connections at the same levels of abstraction are free of other units or include other units. Other skip connections from one level of abstraction to a different level of abstraction may be used. In alternative embodiments, no skip connections between the encoder segment 21 and the decoder segment 23 other than connections at the bottom (i.e., greatest level of abstraction) are provided between the encoder 21 and the decoder 23.

The definition of the neural network arrangement includes an LSTM architecture or unit 29. For example, the neural network is defined as a U-net with a convolutional LSTM architecture at a skip connection 26 or a bottom level of the U-net. FIG. 2 shows the LSTM unit 29 at a bottom of the network architecture for operating on the values of features at a greatest level of compression.

The LSTM unit 29 is a recurrent neural network (RNN) structure for modeling dependencies over time. In addition to relating spatial features to the output segmentation, temporal features are included. The variance over time of pixels, voxels, or groups thereof is accounted for by the LSTM unit 29. The values of the features derived from the pixels, voxels or groups thereof may be different for different images in the sequence. The LSTM unit 29, where positioned to receive feature values rather than input image data, derives values for features based on the variance over time or differences over time (i.e., state information) of the input feature values for each node.

A memory cell acts as an accumulator of the state information. The cell is accessed, written, and cleared by several self-parameterized controlling gates for accumulation or discard of temporal information. Whether the latest cell output is propagated to the final state is further controlled by an output gate. FC-LSTM, a multivariate version of LSTM, may be used. Since imaging data is being used, a convolutional LSTM is used in one embodiment. Convolution may be incorporated into the input and/or state-to-state transitions. The convolutional LSTM unit 29 determines the future state of a certain memory cell by the inputs and past states of the cell and/or local neighbors is space and/or time. Multiple LSTMs may be stacked and temporally concatenated.

In FIG. 2, the convolutional LSTM unit 29 operates on the level with a greatest feature compression. The convolutional LSTM unit 29 receives the output of the encoder segment 21 and passes results or output to the decoder segment 23 (i.e., is between the encoder 21 and the decoder 23). Since, at the end of the encoder 21, the network has extracted the most compressed features carrying global context, the convolutional LSTM unit 29 is positioned at the bottom level of network to extract global features that capture the temporal changes observed over a time window along the cardiac cycle.

The output from the encoder segment 21 may skip the LSTM unit 29 as well so that the decoder segment 23 receives both the output of the LSTM unit 29 and the output of the encoder segment 21. Alternatively, the decoder segment 23 receives only the output of the LSTM unit 29 at this level of feature compression or abstraction.

In other embodiments, the LSTM unit 29 operates on feature values output at a least and/or intermediate level of feature compression or abstraction. A LSTM unit 29 may be positioned for any connection, such as concatenation, between the encoder segment 21 and the decoder segment 23. For example, an LSTM unit 29 is positioned at a skip connection 26. Temporal patterns are identified from features extracted from any level of compression or abstraction in the network encoder 21.

Figure 3:
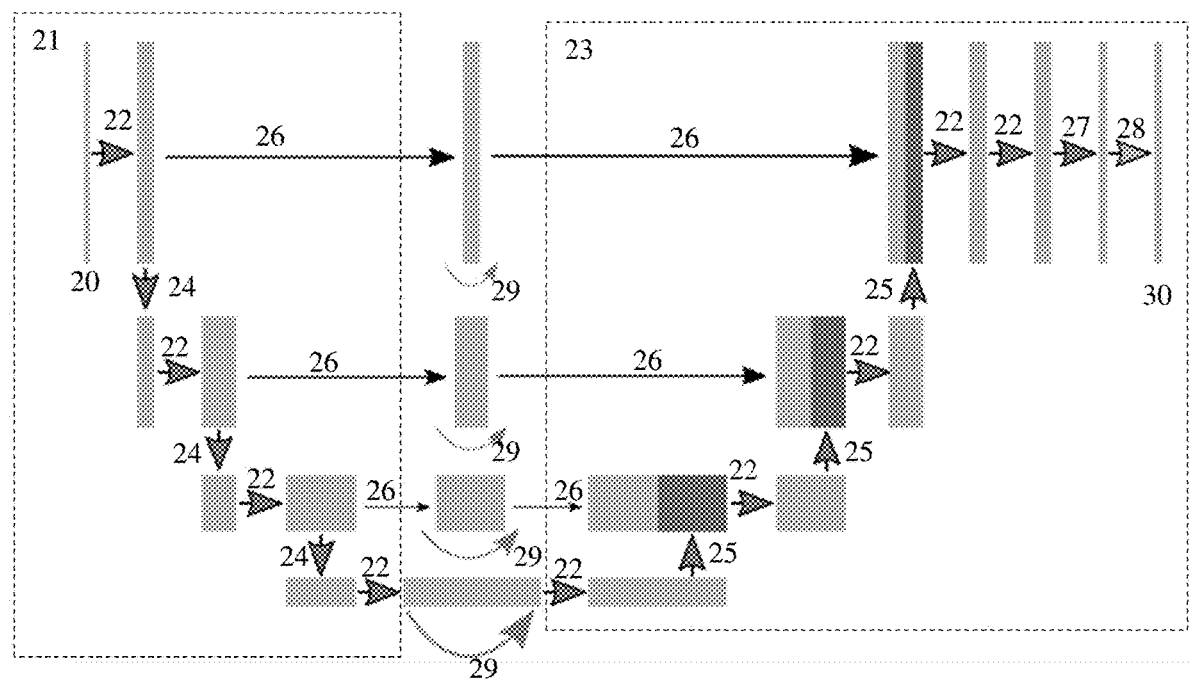
FIG. 3 illustrates an example neural network architecture using LSTM in sequence and at skip connections.

In yet another embodiment, LSTM units 29 are provided for each level of compression/abstraction and/or skip connection 26 and the bottom of the U-net. FIG. 3 shows an example. LSTM units 29 are defined for learning temporal patterns for the most compressed or abstract features at the bottom level of the network as well as temporal patterns from features extracted from every other level of compression or abstraction of the network encoder 21.

Other locations may be provided for the LSTM units 29. For example, the LSTM units 29 operate within the encoder 21 and/or decoder 23. The LSTM units 29 may be between layers or levels of compression or abstration of the encoder 21 and/or decoder 23 instead of or in addition to between the encoder 21 and decoder 23.

To learn to determine patterns over time of the values of features, the LSTM unit 29 uses the spatiotemporal features. The encoder 21 derives values for spatial features for each image in a sequence. The LSTM unit 29 derives values for the spatial features over time through at least part of the sequence. Based on input of the images from different times and the corresponding spatial features, the LSTM unit 29 identifies values for temporal patterns.

Figure 4:
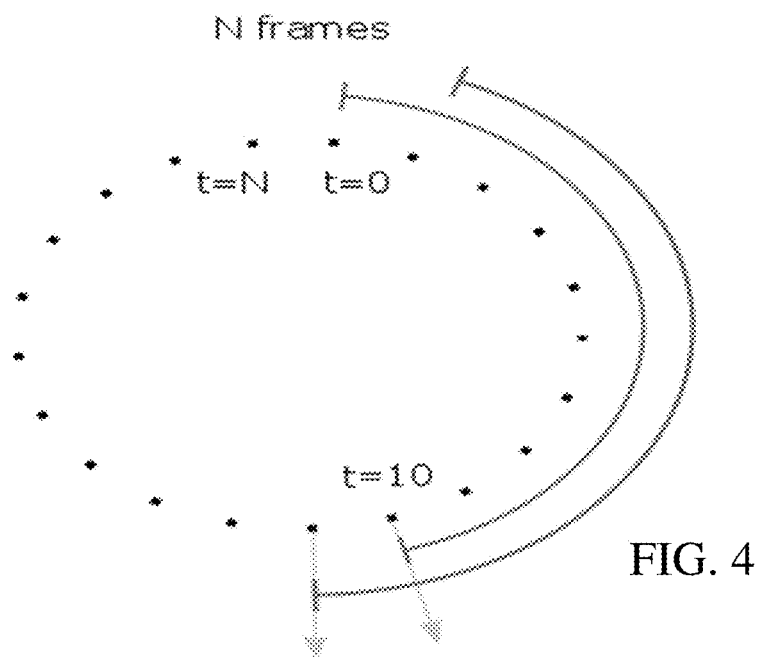
FIG. 4 illustrates example time windowing for LSTM.

The period over which the patterns are derived may be learned and/or set. For example, a time window less than a heart cycle is used, but longer time windows may be used. Different time windows may be used for different nodes and/or LSTM units 29. In one embodiment, 18-35 frames or images are input for each cycle. The time window is 10 frames, but shorter or longer windows may be used. The window moves 1 frame at a time. Since cardiac motion has a cyclic pattern, for an N-frame sequence, the window moves N times with a step size of 1. Each frame appears as the last frame in a window, and each frame appears in N windows (e.g., 10 windows). This approach is shown in FIG. 4 where a cycle is divided into N times where N is greater than 10 (e.g., N=21) and the window is set at 10 times. Other window sizes and/or step sizes may be used. Alternatively, no windowing is used where the temporal variation through the entire temporal collection (e.g., 1 or more cycles) is used.

The neural network is defined to provide a segmentation output. Locations that are members or represent the object are identified. The segmentation may be a binary output per location or may identify a boundary. Where the spatiotemporal input data is slices or 2D planes over time (2D+t or 3D), the segmentation output is a pixel mask for each of the 2D planes. Where the spatiotemporal input data is volumes or 3D frames over time (3D+t or 4D), the segmentation output is a voxel mask for each of the 3D frames or volumes. A binary indication of membership of each pixel or voxel to the object is provided. Other segmentation outputs may be used.

In one embodiment, a SoftMax layer or unit 29 is the last layer of the neural network architecture. Since the task is binary segmentation, the SoftMax layer 28 is added at the end of the network. The SoftMax layer 28 implements binary cross-entropy loss based on the feature values input, but other functions may be used.

In act 14 of FIG. 1, a machine (e.g., image processor, workstation, computer or server) trains the neural network arrangement with the training data having ground truth segmentation of the object. The neural network including LSTM is trained using the medical images of the object and the ground truth annotation for the object. Machine learning is performed to train the various units using the defined deep architecture. The features (e.g., convolution kernels, transposed-convolution kernels, max pooling connections, and binary mapping) that are determinative or map to the ground truth segmentation are learned. The features providing the desired result or detection of the object are learned.

The results relative to the ground truth and the error for reconstruction for the feature learning network are back-projected to learn the features that work best. In one embodiment, a L2-norm loss is used to optimize the network. Other error functions may be used. In one embodiment, the weights of the network are randomly initialized, but another initialization may be used. End-to-end training is performed, but one or more features may be set. Batch normalization, dropout, and data augmentation are not used, but may be. The optimization is with the RMSprop optimizer, but other optimization functions (e.g., Adam, SGD, etc.) may be used. During the optimization, the different distinguishing features are learned. The features providing an indication of location of the object given input medical image sequences are learned.

In act 16, the machine outputs a trained neural network. The machine-learnt network incorporates the deep learned features for the various units and/or layers of the network. The collection of individual features forms a feature or feature set for distinguishing an object from other objects. The features are provided as nodes of the feature units in different levels of abstraction or compression. The nodes define convolution kernels trained to extract the features.

Once trained, a matrix, kernels, or other trained network is output. The data represents the trained architecture. The machine-learnt network includes definitions of convolution kernels and/or other characteristics of the neural network trained to detect the object of interest, such as a left ventricle. Alternatively, separate matrices or network representations are used for any of the nodes, units, layers, network, and/or detector.

The machine-learnt detector is output to a network or memory. For example, the neural network as trained is stored in a memory for transfer and/or later application.

Using the learned features, the machine-learnt network may detect the object of interest in an input series of medical images for a patient. Once the network is trained, the network may be applied. The network with defined or learnt features is used to extract from input images. The machine-learnt network uses the extracted features from the image to detect the object, such as detecting in the form of a spatial distribution or heatmap of likely locations of the object and/or detecting a full segmentation.

FIG. 5 is a flow chart diagram of one embodiment of object detection, such as heart segmentation with a MR imaging system. FIG. 5 shows a method for object (e.g., left ventricle) detection with a medical imaging system, such as a MR system. The machine-learnt network is applied to detect the object.

Figure 7:
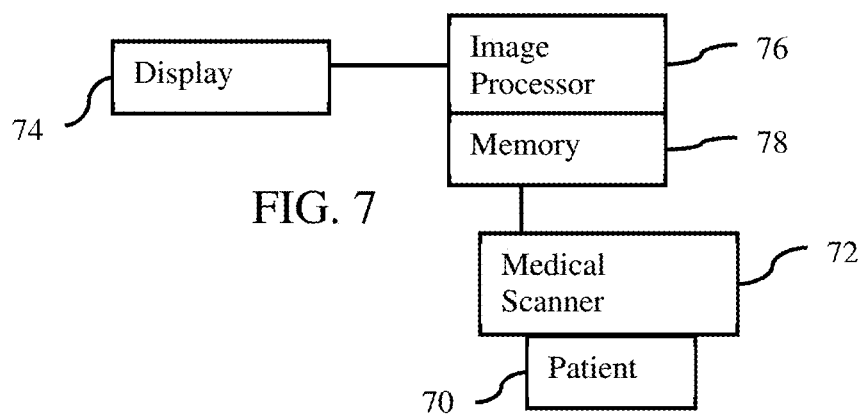
FIG. 7 is a block diagram of one embodiment of a system for segmentation.

The same image processor or a different image processor than used for training applies the learnt features and network. For example, the network architecture, learnt weights, and learnt kernels are transmitted from a graphics processing unit used to train to a medical scanner, medical server, or medical workstation. An image processor of the medical device applies the machine-learnt network. For example, the medical imaging system of FIG. 7 is used.

Additional, different, or fewer acts may be provided. For example, acts for configuring the medical system are provided. The acts are performed in the order shown (top to bottom or numerical), but other orders may be used.

In act 52, the image processor receives a sequence of images of an object. The images are from a scan of a patient. For example, an MR imaging system scans the heart of a patient (e.g., torso, cardiac or heart scan) over time (e.g., one or more heart cycles). The resulting scan data is received from or by the MR system. The scan data is a set of spatiotemporal MR images.

The receipt is by scanning the patient. Alternatively, the receipt is by receiving from a network interface. In other embodiments, receipt is by loading from memory.

The received medical images are to be used to detect the location or locations of the object or objects of interest. The received medical image may be pre-processed, such as normalized in a same way as the training medical images.

In act 54, the medical imaging system detects the locations in images representing the object. For example, the machine-learnt network is applied to determine locations of the left ventricle in one or more (e.g., all) of the images. Other heart regions may be alternatively or additionally segmented. The object is detected using the hidden features of the deep network. For example, the trained convolution units and LSTM units are applied to the scan data or derived feature values to extract the corresponding features and output the binary mask for the object for each of the input images. The features of the input images are extracted from the images. Other more abstract features may be extracted from those extracted features using the architecture. Depending on the number and/or arrangement of units, other features are extracted from features. Other features based on the temporal patterns of extracted features values are calculated using the LSTM units.

For application, the scan data is input to the machine-learnt network. In one embodiment, the machine-learnt network is a fully convolutional network, such as a convolutional-to-transposed-convolutional network with a LSTM network or layer. The machine-learnt network may be a U-net encoder-decoder trained for detection of the heart region. Multiple levels of feature compression or abstraction are provided, such as four. The encoder segment has a plurality of convolutional layers with increasing feature compression or abstraction, and the decoder segment has a plurality of transposed-convolutional layers with decreasing feature compression or abstraction.

The LSTM layer may be a convolutional LSTM. The LSTM operates on the level with a greatest feature compression or abstraction (e.g., bottom of the U-net between the encoder output and the decoder input), finding patterns over time for the most abstract feature values. The LSTM extracts global features that capture the temporal changes observed over a time window over at least part of the cardiac cycle.

In other embodiments, the machine-learnt network includes one or more LSTM layers operating at other levels of compression or abstraxtion, such as at a level of least compression/abstraction and/or intermediate levels of feature compression/abstraction. LSTM layers may operate on each of the levels of compression or abstraction, such as at any skip connections and the bottom connection of U-net between the encoder and the decoder. Spatial-temporal patterns are identified from features extracted from every level of the U-net encoder, by incorporating convolutional LSTM in the skip connections.

Any time window may be used in application. The same time window used in training is applied. For example, a time window less than (e.g., about ½ or ⅓ of the heart cycle) is used in the LSTM. The same time window is applied to each LSTM layer, but different LSTM units may have different window sizes and/or step sizes.

The trained neural network is configured by the machine training to output a heatmap or binary mask at a resolution of the medical images or scan data. For example, the neural network outputs a binary mask indication of locations of the left ventricle. Where a heatmap (e.g., probability by location) is output, thresholding or another image process (e.g., SoftMax) is applied to segment based on the heatmap. The machine-learnt neural network includes an output layer, such as a SoftMax layer, to output the binary mask. Other outputs, such as outputting the heatmap as a segmentation, may be used.

In act 56, the medical imaging system generates an image with information that is a function of the detected heart region. The image is output. The results or segmented information are output.

In one embodiment, one or more medical images with annotations showing position or segmentation of the object are output. An image of the heart of the patient includes highlighting, coloring, brightness, graphics, or other markers showing locations of the detected object. In alternative embodiments, the scan data for the segmented object with other scan data removed is used to generate the image. The segmentation is used to mask or select data to be displayed.

In yet other embodiments, the image shows a value of a quantity where the value is a function of the segmented heart region. For example, volume, volume change, cross-sectional area, ejection fraction, left ventricular mass, wall thickness, wall abnormality measure, and/or other cardiac quantification is calculated. The calculation relies on the location of the object in an image and/or over time. The medical imaging system calculates the quantity using the segmentation. The image is generated with an annotation or other display of the value or values of the quantity or quantities. The image may or may not also include a spatial representation of the heart or segmented object from the scan data.

The use of LSTM in the neural network improves the medical imaging system's ability to segment. U-net is a prevalent segmentation model in medical imaging. The performance of two proposed models (e.g., FIGS. 2 and 3) is compared with U-net (i.e., FIG. 2 without the LSTM unit 29). To improve the baseline, a sequence-to-sequence (i.e., cycle-to-cycle) segmentation with U-net is used. In this variant of U-net, 3D convolution (2D+time) is used, so that U-net also uses the temporal information to some extent.

To evaluate the predicted masks, a dice coefficient is calculated. A higher score indicates better agreement with the ground truth. For training based on images from 89 patients and an 11-test subject partition, the dice scores for these models are provided in Table 1.

TABLE 1

|  | Total | Train | Test |
| --- | --- | --- | --- |
| U-net 3D | 0.9466 | 0.9690 | 0.7424 |
| w/ Conv. LSTM | 0.9344 | 0.9533 | 0.7631 |
| w/ Conv. LSTMs | 0.9451 | 0.9654 | 0.7622 |

In terms of average test dice score, the machine-learnt network with convolution LSTM at the end of the contracting path of U-net (i.e., FIG. 2), performs best. The machine-learnt network with convolution LSTMs at each skip connection and the bottom (i.e., FIG. 3) performs better than U-net 3D.

Figure 6:
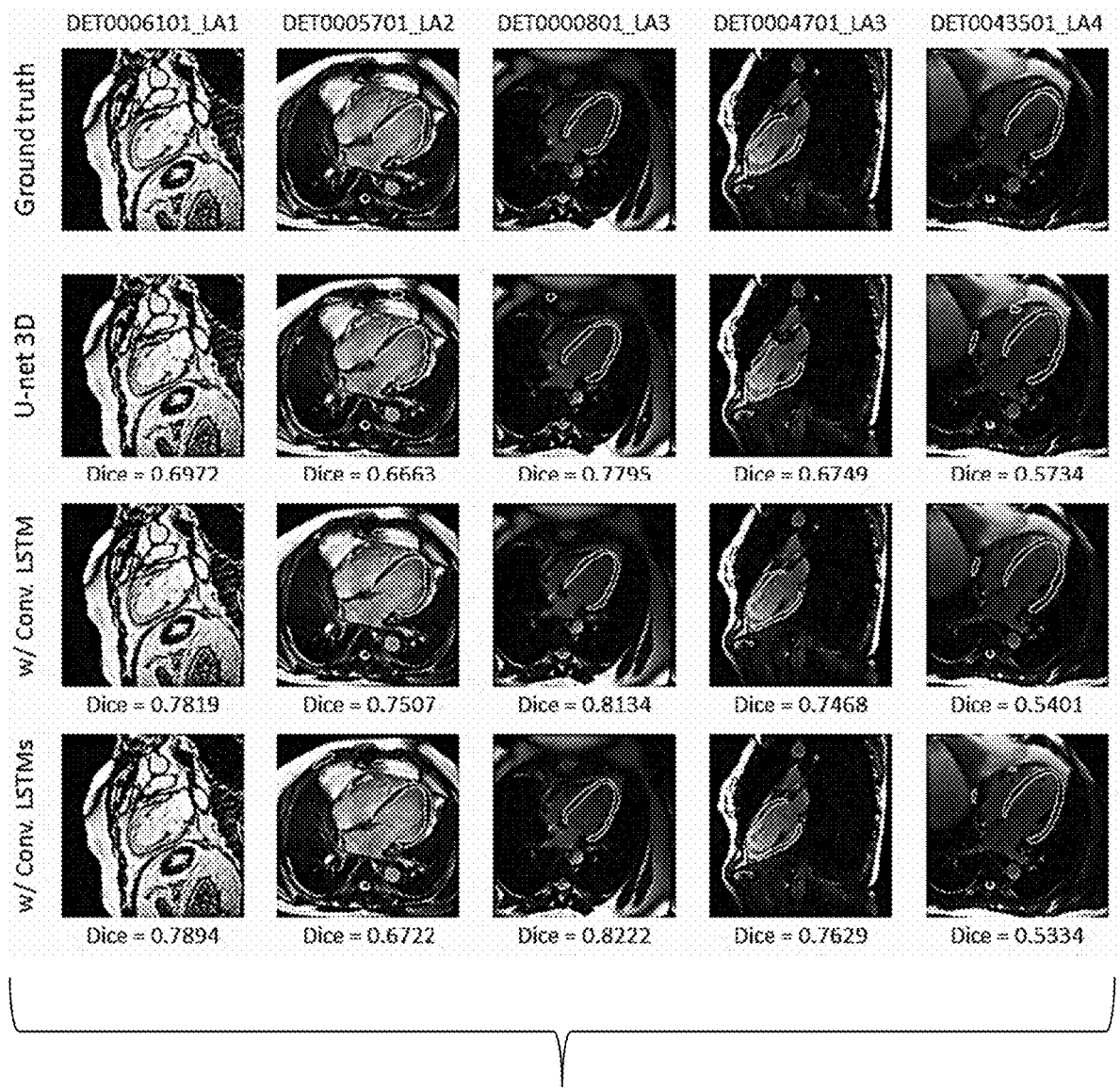
FIG. 6 shows example images with segmented left ventricles.

FIG. 6 shows some of the predicted masks (horseshoe shapes overlaid on cross-sectional 2D MR images) obtained using these three models, along with the ground truth. The masks after using convolutional LSTM are much smoother, and the breakdown in the predicted masks has also reduced significantly (i.e., fewer gaps).

5-fold testing on U-net 3D and the proposed model with convolution LSTM at the bottom level of U-net (i.e., FIG. 2) also shows better performance due to incorporation of the LSTM. The test dice scores over these 5 folds for both models are shown in Table 2, below.

TABLE 2

|  | fold 1 | fold 2 | fold 3 | fold 4 | fold 5 |
| --- | --- | --- | --- | --- | --- |
| U-net 3D | 0.7697 | 0.7440 | 0.7598 | 0.7566 | 0.7570 |
| w/ Conv. LSTM | 0.7778 | 0.7604 | 0.7807 | 0.7813 | 0.7807 |

The proposed model of U-net with convolution LSTM performs consistently better.

The left-ventricle or other heart region segmentation task benefits from leveraging the temporal information available in cardiac images. By incorporating a convolutional LSTM at the bottom level and/or other locations of U-net or other neural networks, segmentation by a machine may be improved. The imaging and/or quantification based on the segmentation output by the medical imaging system may better assist in diagnosis and treatment. Physician-assisted diagnosis and treatment of cardiovascular diseases may be improved, resulting in less review time by physicians.

FIG. 7 shows a medical imaging system for segmentation, such as detection of the left ventricle in MR scan data. The medical imaging system is a host computer, control station, workstation, server, medical diagnostic imaging scanner, or other arrangement used for training and/or application of a machine-learnt network to medical images.

The medical imaging system includes the display 74, memory 78, and image processor 76. The display 74, image processor 76, and memory 78 may be part of the medical scanner 72, a computer, server, or other system for image processing medical images from a scan of a patient. A workstation or computer without the medical scanner 72 may be used as the medical imaging system. Additional, different, or fewer components may be provided, such as including a computer network for remote segmentation of locally captured scans or for local segmentation from remotely captured scans.

The medical imaging system is for training, such as using images from the memory 78 and/or medical scanner 72 as ground truth. Alternatively, the medical imaging system is for application of the machine-learnt network trained with the deep learning in a neural network architecture including LSTM.

The medical scanner 72 is a medical diagnostic MR imaging system. A main magnet or coil generates a substantially uniform magnetic field through the patient 70. Gradient coils, local coils, and/or a whole-body coil generate a pulse sequence to shift spin axes of molecules in the patient away from the uniform magnetic field lines. The local coils and/or whole-body coil detect radio frequency emissions caused by the relaxation of the spin axes of the molecules returning to the magnetic field lines. This k-space data is reconstructed into an object or spatial domain using Fourier processing. The resulting scan data represents the cardiac region of the patient. The pulse sequence may be repeated or continues in order to obtain scan data representing the cardiac region over time. Any MR cardiac imaging pulse sequence or scanning may be used. Other medical scanners may be used instead of the MR scanner, such as ultrasound, computed tomography, positron emission tomography, x-ray, angiography, fluoroscopy, or single photon emission computed tomography.

The image processor 76 is a control processor, general processor, digital signal processor, three-dimensional data processor, graphics processing unit, application specific integrated circuit, field programmable gate array, digital circuit, analog circuit, combinations thereof, or other now known or later developed device for processing medical image data. The image processor 76 is a single device, a plurality of devices, or a network. For more than one device, parallel or sequential division of processing may be used. Different devices making up the image processor 76 may perform different functions, such as an automated anatomy detector and a separate device for generating an image based on the detected object. In one embodiment, the image processor 76 is a control processor or other processor of a medical diagnostic imaging system, such as the medical scanner 72. The image processor 12 operates pursuant to stored instructions, hardware, and/or firmware to perform various acts described herein, such as controlling scanning, segmenting an object from scan data, and/or generating an output image showing a detected object.

The image processor 76 is configured to train a deep architecture. Based on a user provided or other source of the network architecture and training data, the image processor 76 learns features for an encoder and a decoder to train the network. The result of the training is a machine-learnt network for segmenting an object based on the neural network architecture including LSTM.

Alternatively or additionally, the image processor 76 is configured to segment based on the learned features. The image processor 76 is configured to apply a machine-learnt detector to data from the scan of a patient 70 (i.e., image data from the medical scanner 72). The machine-learnt detector has an architecture including convolutional and transposed-convolutional layers and a LSTM layer. In one embodiment, U-net forms the convolutional and transposed-convolutional layers. An encoder segment has convolutional layers with increasing feature compression or abstraction, and the decoder segment has transposed-convolutional layers with decreasing feature compression or abstraction. The LSTM, such as convolution LSTM, is between the encoder segment and the decoder segment. For example, the LSTM receives features from the encoder segment at a greatest of the increasing feature compression or abstraction. As another example, the LSTM receive features from the encoder segment along a skip connection. In yet other examples, LSTM units are at all skip connections and a bottom of the U-net.

Based on application of the scan data representing the cardiac region over time to the machine-learnt detector, the image processor 76 is configured to output a heart segmentation. A part of the heart, such as the left ventricle, as represented in the data from the scanning, is identified.

The image processor 76 may be configured to output an image showing spatial distribution of the object. A sequence of images showing the spatial distribution of the object over time may be output. In other embodiments, the spatial distribution is used to calculate a value for a quantification. The value is output in an image.

The display 74 is a CRT, LCD, projector, plasma, printer, tablet, smart phone or other now known or later developed display device for displaying the output, such as an image with a highlight of a detected object or objects. For example, the display 74 displays a medical image or images with an annotation as a graphic or colorization of the locations of the object as detected. In another example, the annotation or image is an alphanumerical or graphic representation of the quantification based on the segmentation.

The instructions, medical images, network definition, features, machine-learnt detector, outputs, and/or other information are stored in a non-transitory computer readable memory, such as the memory 78. The memory 78 is an external storage device, RAM, ROM, database, and/or a local memory (e.g., solid state drive or hard drive). The same or different non-transitory computer readable media may be used for the instructions and other data. The memory 78 may be implemented using a database management system (DBMS) and residing on a memory, such as a hard disk, RAM, or removable media. Alternatively, the memory 78 is internal to the processor 76 (e.g. cache).

The instructions for implementing the training or application processes, the methods, and/or the techniques discussed herein are provided on non-transitory computer-readable storage media or memories, such as a cache, buffer, RAM, removable media, hard drive or other computer readable storage media (e.g., the memory 78). Computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination.

In one embodiment, the instructions are stored on a removable media device for reading by local or remote systems. In other embodiments, the instructions are stored in a remote location for transfer through a computer network. In yet other embodiments, the instructions are stored within a given computer, CPU, GPU or system. Because some of the constituent system components and method steps depicted in the accompanying figures may be implemented in software, the actual connections between the system components (or the process steps) may differ depending upon the manner in which the present embodiments are programmed.

Various improvements described herein may be used together or separately. Although illustrative embodiments of the present invention have been described herein with reference to the accompanying drawings, it is to be understood that the invention is not limited to those precise embodiments, and that various other changes and modifications may be affected therein by one skilled in the art without departing from the scope or spirit of the invention.

What is claimed is:

1. A method for heart segmentation with a magnetic resonance imaging system, the method comprising:
scanning a heart of a patient over time with the magnetic resonance imaging system;
detecting, by a machine-learnt network, a heart region represented in scan data from the scanning, the machine-learnt network comprising a convolutional to transposed-convolutional network with a convolutional long-short-term memory network within the convolutional to transposed-convolutional network; and
generating an image with information that is a function of the detected heart region.

2. The method of claim 1 wherein scanning comprises acquiring the scan data as spatiotemporal magnetic resonance images.

3. The method of claim 1 wherein detecting by the machine-learnt network comprises detecting with a fully convolutional network.

4. The method of claim 1 wherein detecting by the machine-learnt network comprises detecting with a convolutional encoder-decoder trained for detection of the heart region.

5. The method of claim 1 wherein the machine-learnt network has varying levels of feature abstraction, and wherein detecting by the machine-learnt network comprises detecting with the convolutional long-short term memory network operating on the level with a greatest feature abstraction.

6. The method of claim 5 wherein detecting by the machine-learnt network comprises detecting with the convolutional long-short term memory network operating on each of the levels.

7. The method of claim 1 wherein the machine-learnt network has varying levels of feature abstraction, and wherein detecting by the machine-learnt network comprises detecting with the convolutional long-short term memory network operating on the level with a least or intermediate feature abstraction.

8. The method of claim 1 wherein the convolutional long-short term memory network comprises a time window less than a heart cycle.

9. The method of claim 1 wherein detecting by the machine-learnt network comprises detecting with a SoftMax layer at an output of the machine-learnt network.

10. The method of claim 1 wherein detecting the heart region comprises detecting a left ventricle.

11. The method of claim 1 wherein generating the image comprises generating a magnetic resonance image of the heart of the patient with the detected heart region highlighted.

12. The method of claim 1 wherein generating the image comprises generating the image as showing a value of a quantity, the value being a function of the heart region.

13. A medical imaging system for heart segmentation, the medical imaging system comprising:
 a medical scanner configured to scan a cardiac region of a patient over time;
 an image processor configured to apply a machine-learnt detector to data from the scan, the machine-learnt detector having an architecture including convolutional and transposed-convolutional layers and a long-short-term memory layer within the convolutional and transposed-convolutional layers, the machine-learnt detector configured to output a heart segmentation as represented in the data from the scan; and
 a display configured to display a medical image with an annotation based on the output.

14. The medical imaging system of claim 13, wherein the long-short-term memory layer comprises a convolutional long-short-term memory layer.

15. The medical imaging system of claim 13 wherein the convolutional and transposed-convolutional layers comprise a U-net.

16. The medical imaging system of claim 13 wherein the convolutional and transposed-convolutional layers comprise an encoder segment and a decoder segment, the encoder segment having a plurality of convolutional layers with increasing feature abstraction and the decoder segment having a plurality of transposed-convolutional layers with decreasing feature abstraction.

17. The medical imaging system of claim 16 wherein the long-short-term memory layer is between the encoder segment and the decoder segment, receiving features from the encoder segment at a greatest of the increasing feature abstraction.

18. The medical imaging system of claim 16 wherein the long-short-term memory layer is between the encoder segment and the decoder segment at a skip connection.

19. A method for machine training for heart segmentation, the method comprising:
 defining a neural network arrangement with a convolutional long-short-term memory architecture;
 training, by a machine, the neural network arrangement with training data having ground truth segmentation of the heart segmentation in spatiotemporal images, the ground truth segmentation for the training of the neural network arrangement having segmentations over time so that the convolutional long-short-term memory architecture is trained to operate on information from different times; and
 storing the neural network as trained.

20. The method of claim 19 wherein defining comprises defining the neural network as a convolutional encoder-decoder with the convolutional long-short-term memory architecture at a skip connection or a bottom layer of the convolutional encoder-decoder.

* * * * *